United States Patent
Montes de Oca

(10) Patent No.: US 10,946,120 B2
(45) Date of Patent: Mar. 16, 2021

(54) LUBRICIOUS URINARY CATHETERS HAVING VARYING FLEXIBILITY

(71) Applicant: Hollister Incorporated, Libertyville, IL (US)

(72) Inventor: Horacio Montes de Oca, Ballina (IE)

(73) Assignee: Hollister Incorporated, Libertwille, IL (US)

( * ) Notice: Subject to any disclaimer, the term of this patent is extended or adjusted under 35 U.S.C. 154(b) by 371 days.

(21) Appl. No.: 15/543,839

(22) PCT Filed: Jan. 20, 2016

(86) PCT No.: PCT/US2016/014034
§ 371 (c)(1),
(2) Date: Jul. 14, 2017

(87) PCT Pub. No.: WO2016/118569
PCT Pub. Date: Jul. 28, 2016

(65) Prior Publication Data
US 2017/0368232 A1    Dec. 28, 2017

Related U.S. Application Data

(60) Provisional application No. 62/232,919, filed on Sep. 25, 2015, provisional application No. 62/106,446, filed on Jan. 22, 2015.

(51) Int. Cl.
*A61L 29/04* (2006.01)
*A61L 29/14* (2006.01)
*A61M 25/00* (2006.01)
*A61M 27/00* (2006.01)

(52) U.S. Cl.
CPC .......... *A61L 29/041* (2013.01); *A61L 29/141* (2013.01); *A61M 25/0054* (2013.01); *A61M 27/00* (2013.01); *A61M 25/0017* (2013.01); *A61M 2210/1096* (2013.01)

(58) Field of Classification Search
CPC ............... A61L 29/041; A61L 29/141; A61M 2210/1096; A61M 25/0017; A61M 25/0054; A61M 27/00; C08L 29/04
See application file for complete search history.

(56) References Cited

U.S. PATENT DOCUMENTS

| | | | |
|---|---|---|---|
| 2,509,241 A * | 5/1950 | Mende ................... A61F 13/26 | 604/11 |
| 2,948,697 A | 8/1960 | Robertson | |
| 4,402,319 A | 9/1983 | Handa et al. | |
| 4,734,941 A * | 4/1988 | DeWitt ................ A61F 5/4556 | 4/144.2 |
| 5,049,138 A * | 9/1991 | Chevalier ............. A61L 29/041 | 604/265 |
| 5,106,890 A * | 4/1992 | Maruhashi ......... A01G 13/0237 | 428/424.6 |
| 5,308,342 A | 5/1994 | Sepetka et al. | |
| 5,484,565 A * | 1/1996 | Larsen ..................... A61L 29/14 | 264/230 |
| 5,601,538 A | 2/1997 | Deem | |
| 5,800,412 A | 9/1998 | Zhang et al. | |
| 5,938,653 A | 8/1999 | Pepin | |
| 6,184,261 B1 * | 2/2001 | Biby ....................... C08J 9/0061 | 521/138 |
| 6,544,451 B1 * | 4/2003 | Heitner ....................... C08J 5/18 | 264/102 |
| 6,579,277 B1 | 6/2003 | Rabiner et al. | |
| 7,112,298 B2 | 9/2006 | Kampa et al. | |
| 8,143,368 B2 | 3/2012 | Domb et al. | |
| 8,187,254 B2 | 5/2012 | Hissink et al. | |
| 2002/0135098 A1 * | 9/2002 | Kawai ...................... C08J 3/005 | 264/143 |
| 2002/0156452 A1 * | 10/2002 | Pursley ............. A61M 25/0017 | 604/500 |
| 2002/0182348 A1 * | 12/2002 | Fujiwara ................... C08F 8/12 | 428/35.2 |
| 2003/0028176 A1 * | 2/2003 | Berg ....................... A61F 13/26 | 604/385.18 |
| 2003/0108705 A1 * | 6/2003 | Duffield ............. B65D 81/3283 | 428/36.6 |
| 2004/0193143 A1 * | 9/2004 | Sauer ................ A61M 25/0054 | 604/544 |
| 2005/0001348 A1 * | 1/2005 | Kohnen ................. C08K 5/053 | 264/211 |
| 2005/0283111 A1 | 12/2005 | Maurice | |
| 2006/0257596 A1 * | 11/2006 | Catalfamo ................ A23F 5/36 | 428/34.1 |
| 2007/0043333 A1 | 2/2007 | Kampa et al. | |
| 2007/0129690 A1 | 6/2007 | Rosenblatt et al. | |
| 2007/0148384 A1 * | 6/2007 | Bowden ..................... C08L 3/02 | 428/35.7 |
| 2007/0178299 A1 * | 8/2007 | Verrall ................... C08K 5/053 | 428/323 |
| 2007/0259996 A1 * | 11/2007 | Vicari ................ C08K 5/34924 | 524/56 |

(Continued)

FOREIGN PATENT DOCUMENTS

JP           06007426 A      1/1994
WO     WO 2007/028058 A2   3/2007
(Continued)

OTHER PUBLICATIONS

Wright, E.J., et al.; "Tensile Analysis and Swelling Characterisation Of Co-Solvent Effects In Poly(Vinyl Alcohol) Films", Journal of Pharmacy and Pharmacology, vol. 62, No. 10, 2010, pp. 1351-1352.
(Continued)

*Primary Examiner* — Adam Marcetich
(74) *Attorney, Agent, or Firm* — Cook Alex Ltd.

(57) ABSTRACT

A catheter having a shaft made from polyvinyl alcohol where in the shaft has a varying stiffness along the length of the shaft.

14 Claims, No Drawings

(56) References Cited

U.S. PATENT DOCUMENTS

| | | | |
|---|---|---|---|
| 2008/0009584 A1* | 1/2008 | Catalfamo | B65D 65/46 525/56 |
| 2008/0108748 A1* | 5/2008 | Buckley | C08L 29/04 524/612 |
| 2008/0200597 A1 | 8/2008 | Morris | |
| 2009/0286906 A1* | 11/2009 | Shi | C08J 5/18 524/47 |
| 2009/0286908 A1* | 11/2009 | Kwak | C08F 14/06 524/48 |
| 2009/0317768 A1* | 12/2009 | Mayer | A61B 17/68 433/201.1 |
| 2010/0213091 A1* | 8/2010 | Kim | B32B 15/08 206/438 |
| 2010/0217184 A1 | 8/2010 | Koblish et al. | |
| 2010/0248861 A1* | 9/2010 | Mo | B29C 45/0001 473/351 |
| 2011/0060313 A1 | 3/2011 | Liu et al. | |
| 2011/0071507 A1 | 3/2011 | Svensson et al. | |
| 2011/0166056 A1* | 7/2011 | Huber | C11D 17/042 510/224 |
| 2011/0270228 A1 | 11/2011 | Haslinger et al. | |
| 2012/0302952 A1* | 11/2012 | Kitada | A61M 25/0021 604/96.01 |
| 2013/0012923 A1 | 1/2013 | Baxter et al. | |
| 2013/0123752 A1* | 5/2013 | Pursley | A61M 25/0009 604/528 |
| 2013/0214456 A1* | 8/2013 | Kanade | B01F 3/1221 264/328.18 |
| 2013/0245551 A1 | 9/2013 | O'Day | |
| 2013/0245610 A1 | 9/2013 | Haslinger et al. | |
| 2015/0148461 A1* | 5/2015 | Wang | C08L 1/284 524/43 |
| 2015/0174368 A1* | 6/2015 | Garrison | A61M 25/0054 604/525 |

FOREIGN PATENT DOCUMENTS

| | | |
|---|---|---|
| WO | 2014077886 A1 | 5/2014 |
| WO | WO 2015/089181 A2 | 6/2015 |

OTHER PUBLICATIONS

PCT Notification concerning transmittal of International Preliminary report on patentability and PCT Written Opinion of the International Searching Authority, PCT Application No. US2016/014034 dated Aug. 3, 2017.

Australian Examination Report No. 1 for Australian Patent Application No. 2016209433 entitled: Lubricious Urinary Catheters Having Varying Flexibility, dated Apr. 12, 2019, pp. 1-8.

* cited by examiner

LUBRICIOUS URINARY CATHETERS HAVING VARYING FLEXIBILITY

The present application is the U.S. National Stage of PCT International Patent Application No. PCT/US2016/014034, filed Jan. 20, 2016, which claims the benefit of and priority to U.S. Provisional Application No. 62/106,446, filed Jan. 22, 2015, and claims the benefit of and priority to U.S. Provisional Patent Application No. 62/232,919, filed Sep. 25, 2015, all of which are hereby incorporated herein by reference.

TECHNICAL FIELD

The present disclosure generally relates to urinary catheters. More particularly, the present disclosure relates to lubricous urinary catheters having a varying flexibility along their length and even more particularly to lubricious flushable catheters having varying flexibility.

BACKGROUND

Catheters are used to treat many different types of medical conditions and typically include an elongated shaft that is inserted into and through a passageway or lumen of the body. Catheters, and in particular intermittent catheters, are commonly used by those who suffer from various abnormalities of the urinary system, such as urinary incontinence. With the advent of intermittent catheters, individuals with urinary system abnormalities can self-insert and self-remove intermittent catheters several times a day.

Catheters are commonly made from polymers, such as polyvinyl chloride (PVC), thermoplastic elastomers (TPE) and polyurethane (PU). It is common to lubricate such catheters so as to reduce friction to allow for easier and less traumatic insertion and withdrawal of the catheter. Currently, there are two main categories of lubricated catheters, namely gel lubricated catheters and hydrophilic coated catheters.

Gel lubricated catheters are made easier to insert and withdraw by application of a water-based lubricant on the outer surface of the catheter. A catheter can be supplied with lubricant which is applied on the outer surface just before or during the packaging operation. Alternatively, a user can apply lubricant to the catheter surface just prior to the catheter being inserted into the urethra. However, the handling of gel lubricated catheters by the user can be messy, leaving lubricant on the user's hands. Further, it can increase the risk of infection from microorganisms being introduced into the body through handling of the gel lubricated catheter.

In a hydrophilic coated catheter, the catheter is provided with a thin hydrophilic coating which is applied to the outer surface of the catheter during its manufacture. The coating is activated by swelling the hydrophilic coating with a hydrating agent such as liquid water, water vapor, combinations thereof and the like to provide an extremely low coefficient of friction surface. The most common form of this product is one in which a sterile, individually packaged, single use catheter is provided in a dry state or condition. The user opens the package, pours water into the package, waits a predetermined period of time, for example, 30 seconds, and then removes the catheter from the package which is ready for insertion. Some hydrophilic coated catheters are provided in a package that contains enough liquid water to cause it to be immersed. Others are provided with a separate packet of water within the package wherein the packet contains a sufficient amount of water necessary to immerse the catheter within the package. In this type of package, the packet is burst open within the package just prior to use.

One disadvantage of the hydrophilic coated catheters which are wetted through immersion in a liquid is that the liquid has a tendency to spill from the package as the user handles the catheter and tries to remove it from the package for subsequent insertion. Further, special packaging requirements increase the complexity of such catheter systems. Another disadvantage of the hydrophilic coated catheter is that the catheter has an extremely slippery surface which makes it quite difficult for the user to handle during insertion.

Interest has been increasing in flushable catheters, which may be disposed of by flushing down the toilet. Flushable catheters may be made from water soluble polymers or polymers that disintegrate, degrade or break up in water. Gel lubricants and hydrophilic coatings may not be suitable for use with catheters made of such water soluble materials due to the material's sensitivity to water.

Additionally, medical catheters typically include a shaft that is sufficiently flexible to navigate the curves of a body lumen (especially urinary catheters intended for male users), yet rigid enough to be pushed through the urethra without collapsing or buckling before an end of the catheter reaches the bladder.

Therefore, there is a need for improved catheters having a lubricious surface without the user having to handle gel-lubricants and without the risk of water spillage while opening the package or activating the hydrophilic surface and for the catheter to have sufficient flexibility to navigate the curves of a body lumen.

The present disclosure provides urinary catheters with one or more of improved flexibility/rigidity, lubricity and/or flushable characteristics.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, the present disclosure provides a urinary catheter including a shaft made of polyvinyl alcohol. The shaft includes a first section having a first stiffness and a second section having a second stiffness.

In another aspect, a urinary catheter includes a shaft made of polyvinyl alcohol wherein the shaft includes a first section having a first stiffness and a second section having a second stiffness, and at least one of said sections is impregnated with a plasticizing agent In another aspect, a urinary catheter including a shaft made from polyvinyl alcohol wherein the shaft has a first section and a second section. The first section of the shaft has an amount of plasticizing agent absorbed therein and the second section of the shaft has a second amount of plasticizing agent absorbed therein wherein the second amount of plasticizing agent is different from the first amount.

In yet another aspect, a urinary catheter includes a catheter shaft having a first section comprised of polyvinyl alcohol and a first amount propylene glycol and a second section comprised of polyvinyl alcohol and a second amount of propylene glycol wherein the first section has a different stiffness from the second section.

In another aspect, a method of making a catheter of varying stiffness is provided. The method includes immersing a first section of a catheter made from polyvinyl alcohol in a first plasticizing agent and immersing a second section of the catheter made in a second plasticizing agent.

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The present disclosure is directed to medical devices that include shafts or tubes that may be inserted into and advanced within a lumen of a body, such as a urethra, esophagus, or fallopian tube. Such medical devices include urinary catheters, endoscopes, exploratory and biopsy devices, etc.

The medical devices of the present disclosure include tubes that are made from a water soluble material(s) which may be placed into the sewer system for disposal thereof, e.g. flushed down a toilet. When placed in the sewer system, the water soluble materials of the tubes are dissolved or broken up by the water within the sewer system.

The stiffness of the tubes disclosed herein may vary along the length of the tube which may assist in navigation of the tube through curves and restrictions of a body lumen. Furthermore, the tubes may also be lubricous so as to ease advance and withdrawal of the tube into and from the body lumen. While the embodiments set forth below may be described in the context of urinary catheters, the disclosure is not limited to such and the features disclosed herein may be applicable to any medical tubing that is inserted into a body lumen.

In one embodiment of the present disclosure a urinary catheter includes a catheter shaft that has a proximal insertion end portion and a distal end portion. The proximal insertion end portion of catheter shaft includes eyelets or drainage openings for draining urine from the bladder. The distal end portion of the catheter shaft may have a drainage member, such as a funnel, associated therewith. The drainage member may be integral with the catheter shaft or may be attached to the catheter shaft. The catheter shaft is a tube that has a lumen extending therethrough for the passage of urine from the eyelets to the drainage member.

The catheter shaft may be made from polyvinyl alcohol (PVOH), which may be a warm or cold water soluble PVOH or a mixture thereof. The catheter shaft may also be made from a mixture of PVOH with other polymers or additives. The catheter shaft and the materials thereof (i.e., PVOH with or without other polymers or additives) are preferably suitable for being flushed down the toilet for disposal of the catheter. Furthermore, the drainage portion of the catheter may also be made of flushable material, such as a water soluble material and for example PVOH.

In one embodiment, the PVOH of the catheter shaft may be impregnated with a plasticizing agent that causes plasticization of the PVOH to reduce the stiffness/increase the flexibility of the PVOH catheter shaft. The plasticizing agent may be, for example, a non-solvent of PVOH, a PVOH solvent or a mixture thereof. Such plasticizing agents may include, for example, those disclosed in U.S. Pat. No. 2,948,697 to Robertson et al., which is incorporated herein by reference. In one embodiment, the plasticizing agent is a non-solvent of PVOH, such as propylene glycol. In another embodiment, the plasticizing agent is a mixture of a non-solvent of PVOH and a PVOH solvent such as a mixture of propylene glycol and water. Such mixture may include between about 99%-about 60% propylene glycol by volume (vol %) and about 1 vol %-about 40 vol % of water. For example, the mixture may include 90 vol % propylene glycol and 10 vol % water; 80 vol % propylene glycol and 20 vol % water; 70 vol % propylene glycol and 30 vol % water; or 60 vol % propylene glycol and 40 vol % water.

The catheter shafts may be impregnated with the plasticizing agent by soaking the catheter shafts or portions thereof in the plasticizing agent for a selected time period. The amount of plasticizing agent impregnated within the catheter shaft and/or the amount of plasticization that occurs can depend on several factors including but not limited to the length of soaking time and/or the concentration of the components within the plasticizing agent. The selected soaking time could be from a few minutes to several hours depending on the desired results, temperature and degree of hydrolysis of the polyvinyl alcohol material. In one embodiment, the entire catheter is impregnated with a plasticizing agent by immersing the entire catheter shaft within the plasticizing agent. In other embodiments, different sections of the catheter shaft may be impregnated with different plasticizing agents or impregnated with different amounts/concentrations of the same plasticizing agent. For example, a first section of the catheter may be immersed within a first plasticizing agent for a selected time period and another portion may be immersed in a second, different plasticizing agent for a selected period of time. In yet another embodiment, a first section of the catheter may be immersed within a plasticizing agent for a first period of time and a second section of the catheter shaft may be immersed in the same plasticizing agent for a second period of time that is different from the first period of time. In yet another embodiment, one section of the catheter may be impregnated with a plasticizing agent while another section is not impregnated with any plasticizing agent.

The impregnated catheter shafts may weigh between about 10% and about 100% of the original weight of the catheter shaft. Preferably, the catheter shafts weigh between 5% and 40% of the original weight of the catheter shafts.

In one particular example, the proximal insertion end of a catheter may be impregnated with a plasticizing agent to cause plasticization of the material of the proximal insertion end of the catheter so that the proximal insertion end is more flexible than a portion of the catheter shaft distal of the proximal end portion. This distal portion, which is relatively stiffer than the proximal end portion, may or may not be impregnated with a plasticizing agent. If impregnated with a plasticizing agent, this distal portion may be impregnated with a different plasticizing agent or a different amount of plasticizing agent. In another embodiment, the distal end portion may be impregnated with a plasticizing agent so that the distal end portion is more flexible than a portion of the catheter shaft proximal the distal end portion. This proximal portion, which is relatively stiffer than the distal end portion, may or may not be impregnated with a plasticizing agent. The difference in stiffness between the proximal and distal end portions may make it easier to navigate the catheter shaft through the curves and restrictions of the urethra, e.g., past the prostate.

In some embodiments, the plasticizing agent may also function as a lubricant that causes or provides lubricity to the outer surface of the catheter. For example, catheter shafts soaked in propylene glycol or mixtures of propylene glycol and water have a lubricous outer surface that eases advancement of the catheter shaft through the urethra without the need for additional lubricant. However, additional lubricant may be used if desired. In other embodiments, the catheter may be lubricated in some other manner, such as will a gel or hydrophilic coating.

In one embodiment, the catheter shaft is made of a water soluble PVOH that may be disposed of by flushing down the toilet, such as Mowiflex TC 251 or Mowiflex TC 232 supplied by Kuraray. The PVOH may be formed into the catheter shaft by any suitable process such as by extrusion, injection molding or by the ejection process set forth in WO2014/052770, which is incorporated herein by reference. The PVOH catheter shaft or sections thereof may be impregnated with one or more plasticizing agents to reduce the stiffness/increase the flexibility of the catheter or sections thereof. For example, a first section of the PVOH catheter shaft may be immersed in a plasticizing agent including a mixture of propylene glycol and water wherein the propylene glycol is 90 vol % and the water is 10 vol % of the mixture. This first section of the shaft may be immersed in the plasticizing agent for up to about 24 hours, wherein the immersed shaft is impregnated with the plasticizing agent and gains about 10% of its original weight. A second section of the shaft may be immersed in a plasticizing agent including a mixture of propylene glycol and water wherein the propylene glycol is 80 vol % and the water is 20 vol % of the mixture. This second section of the shaft may be immersed in this plasticizing agent for up to about 24 hours, wherein the immersed shaft is impregnated with the plasticizing agent and gains about 30% of its original weight. Depending on the desired result, the first and second sections may be immersed in the respective plasticizing agent for more than 24 hours, if desired. In this embodiment, the first section of the catheter tube has a relatively greater stiffness than the second section. Additionally, the catheter shaft may have a coefficient of friction of about 0.2 or less.

In another embodiment, the propylene glycol may be compounded with the PVOH prior to forming compounded material into a catheter, by for example, injection molding or extrusion. For instance, PVOH may be compounded with propylene glycol in a twin extruder to form the compounded material. In one embodiment, the propylene glycol is between about 10 wt % to about 40 wt % of the compounded material. For example, the propylene glycol may be about 30 wt % of the compound. The compounded material thus formed may then be formed into a catheter or other medical device.

EXAMPLES

Example 1

PVOH catheter tubes were made from PVOH supplied by Kuraray and sold under trade name Mowiflex TC232. The tubes were produced by the ejection process disclosed in WO2014052770, which is hereby incorporated by reference.

A first half of the tube was immersed at room temperature (substantially 23° C.) for 1 day (about 24 hours) in a mixture of propylene glycol (PG) and water wherein the mixture was 90 vol % PG and 10 vol % water. The immersed tube absorbed liquid and gained approximately 10% in weight.

The second half of the tube was immersed at room temperature (substantially 23° C.) for 1 day (about 24 hours) in a mixture of PG 80 vol % and water 20 vol %. The immersed tube again absorbed liquid and gained. The resulting tube had two distinct portions of differing stiffness wherein the first half of the tube (immersed in PG/water at 90 vol %/10 vol %) was more rigid than the second half of the tube.

Example 2

In Example 2, the above-discussed ejection processes was used to make PVOH tubes for two different types of PVOH. The first set of tubes was made from PVOH sold under the trade name Mowiflex TC 232, supplied by Kuraray. The second of tubes was made from PVOH sold under the trade name Mowiflex TC 251, also supplied by Kuraray.

Tubes from each of the different sets were placed in one of: (1) 100% propylene glycol, (2) a mixture of 90 vol % propylene glycol and 10 vol % water, (3) a mixture of 80 vol % propylene glycol and 20 vol % water or (4) a mixture of 70 vol % propylene glycol and 30 vol % water. The PVOH tubes were placed in the respective liquid(s) for a period of seven days. The tubes were weighed on days 0, 1, 2, 3, 6 and 7 to measure the amount of liquid uptake that occurred during that time period. Below are the results from this Example.

TABLE 1

Percent Mass Change of Mowiflex TC 232

| Time [days] | 100% PG/ 0% water | 90% PG/ 10% water | 80% PG/ 20% water | 70% PG/ 30% water |
|---|---|---|---|---|
| 0 | 0.0% | 0.0% | 0.0% | 0.0% |
| 1 | 4.0% | 11.0% | 27.5% | 57.1% |
| 2 | 5.4% | 14.0% | 35.6% | 76.6% |
| 3 | 6.5% | 17.9% | 48.7% | 117.4% |
| 6 | 8.7% | 23.6% | 77.7% | 201.7% |
| 7 | 9.5% | 25.7% | 91.2% | 237.8% |

TABLE 2

Percent Mass Change of Mowiflex TC 251

| Time [days] | 100% PG/ 0% water | 90% PG/ 10% water | 80% PG/ 20% water | 70% PG/ 30% water |
|---|---|---|---|---|
| 0 | 0.0% | 0.0% | 0.0% | 0.0% |
| 1 | 2.5% | 10.8% | 33.5% | 51.0% |
| 2 | 3.1% | 14.1% | 44.9% | 71.2% |
| 3 | 4.1% | 18.6% | 62.7% | 102.4% |
| 6 | 5.8% | 26.6% | 95.8% | 153.5% |
| 7 | 6.4% | 29.9% | 107.7% | 171.8% |

The greater the gain in weight, the more plasticized the tube became. It was observed that the ratio of propylene glycol to water affected the rates or speeds of plasticization of the tubing. For example, a higher concentration of water resulted in more plasticization which results in a more flexible tube. Similarly, a longer soak time in the liquid also resulted in more plasticization and a more flexible tube. This is an indication that the mechanical properties of the tubing can be controlled from rigid to plastic to gel by varying the concentration of water and/or the length of dwell time in the liquid. After removal from liquid, the tubes retained their flexibility for several days.

Example 3

PVOH plaques were made from PVOH supplied by Kuraray and sold under trade name Mowiflex TC232.

PVOH was compounded with propylene glycol using a Rondol 21 mm twin screw extruder with a 40 L/D. PVOH chips were fed through a gravimetric feeder into the extruder at the standard feed throat (zone 0). Propylene glycol was fed into the extruder with a calibrated pump through zone 1. The compound was extruded onto a moving belt and cooled by air. The compound has about 30 wt % propylene glycol. The solidified extruded strands were fed into a standard pelletizer.

One set of injection molded plaques were produced form the compounded PVOH chips having 30 wt % propylene glycol. A second set of plaques was produced from only PVOH, i.e., having no propylene glycol. An Engle VC200-50 injection molding machine with a screw diameter of 25 mm was utilized. The melt was injected at 200° C. into a rectangular mold at 40° C., producing plaques rectangular plaques 13 cm long, 2.5 cm wide and 0.2 cm thick.

A first sample of plaques made from only PVOH were immersed in a solution of 80% in volume of propylene glycol and 20 vol % water for 8 hours at room temperature. The samples were removed from the solution and the excess liquid removed from the surface with a tissue prior to dynamic mechanical analysis testing (DMA).

A second sample of plaques made from only PVOH were immersed in 100% propylene glycol at room temperature for several days. Samples were removed from the propylene glycol and the excess liquid removed from the surface with a tissue prior to DMA testing.

The storage (shear) modulus of plasticized and un-plasticized plaques was measured by DMA using a Q800 TA Instrument Dynamic Mechanical Analyzer. The cantilever test mode at a frequency of 1 Hz, amplitude of 40 micrometers and a distance of 17 mm between the support jaws was used. The dynamic mechanical load was applied at the middle point between the jaws and onto a specimen having dimensions 2 mm thick, 6 mm wide and 33 mm long, cut from the injection molded plaques.

The percent of gained weight was measured after immersion of the PVOH plaques in 100% PG and a solution of 80/20 PG/water. The excess liquid removed from the surface with a tissue prior to measuring the weight.

Table 3 shows the summary of the results of shear storage modulus (G') and percent of PG uptake at room temperature for plaques immersed in 100% PG for up to 27 days. As can be seen the storage modulus decreases very rapidly after 4 days immersion at levels of after 20 days, with very little change thereafter.

TABLE 3

Shear storage modulus (G') at 25° C. and percent of propylene glycol uptake relative to the weight of the dry PVOH plaques immersed in 100% propylene glycol as a function of immersion time.

| Immersion time [days] | G' [MPa] | PG uptake [%] |
|---|---|---|
| 0 (dry) | 3811 | 0 |
| 4 | 454 | 13.4 |
| 16 | 136 | 25 |
| 17 | 95 | 29 |
| 20 | 51 | 30 |
| 27 | 52 | 34 |

Table 4 shows the summary of the results of shear storage modulus (G') and percent propylene glycol/water uptake at room temperature for plaques immersed in a solution 80/20 propylene glycol/water for up to 12 hours. As can be seen the storage shear modulus decreases very rapidly after 6 hours immersion and reaches a value of 56 MPa and 38% uptake after 12 hours.

TABLE 4

Shear storage modulus (G') at 25° C. and percent of propylene glycol/water uptake relative to the weight of the dry PVOH plaques immersed in 80/20 propylene glycol/water as a function of immersion time

| Immersion time [hours] | G' [MPa] | PG/water uptake [%] |
|---|---|---|
| 0 | 3811 | 0 |
| 6 | 245 | 28 |
| 12 | 56 | 38 |

Injection molded PVOH plaques with nominally 30% propylene glycol (propylene glycol and PVOH compounded using a twin screw extruder) showed a shear storage modulus at 25° C. of G'=25 MPa.

Aspects of the present subject matter described above may be beneficial alone or in combination with one or more other aspects. Without limiting the foregoing description, in accordance with a first aspect, a urinary catheter comprising: a shaft made of polyvinyl alcohol, the shaft including a first section having a first stiffness and a second section having a second stiffness, wherein at least one of said sections is impregnated with a plasticizing agent.

Aspect 2. The urinary catheter of aspect 1, wherein the first section has greater stiffness than the second section.

Aspect 3. The urinary catheter of aspect 1, wherein the second section has a greater stiffness than the first section.

Aspect 4. The urinary catheter of any one of aspects 1-3, wherein the first section is impregnated with the plasticizing agent.

Aspect 5. The urinary catheter of any one of aspects 1-4, wherein the second section is impregnated with the plasticizing agent.

Aspect 6. The urinary catheter of any one of aspects 1-5, wherein the plasticizing agent lubricates the catheter.

Aspect 7. The urinary catheter of any one of aspects 1-6 wherein the plasticizing agent comprises a solvent for polyvinyl alcohol.

Aspect 8. The urinary catheter of any one of aspects 1-7 wherein the plasticizing agent comprises water.

Aspect 9. The urinary catheter of any one of aspects 1-8 wherein the plasticizing agent comprises a non-solvent for polyvinyl alcohol.

Aspect 10. The urinary catheter of any one of aspects 1-9 wherein the plasticizing agent comprises propylene glycol.

Aspect 11. The urinary catheter of any one of aspects 1-6, wherein the plasticizing agent comprises of a mixture of a solvent and non-solvent for polyvinyl alcohol.

Aspect 12. The urinary catheter of aspect 11, wherein the ratio of the solvent to non-solvent is one of 100 vol % non-solvent and 0 vol % solvent; 90 vol % non-solvent and 10 vol % solvent; 80 vol % non-solvent and 20 vol % solvent; and 70 vol % non-solvent and 30 vol % solvent.

Aspect 13. The urinary catheter of any one of aspects 11-12 wherein the solvent comprises water.

Aspect 14. The urinary catheter of any one of aspects 11-13, wherein the non-solvent comprises propylene glycol.

Aspect 15. A urinary catheter, comprising: a shaft made from polyvinyl alcohol, the shaft having a first section and a second section; the first section of the shaft having an amount of plasticizing agent absorbed therein; and the second section of the shaft having a second amount of plasticizing agent absorbed therein, wherein the second amount of plasticizing agent is different from the first amount.

Aspect 16. The urinary catheter of aspect 15 wherein the plasticizing agent comprises a solvent for polyvinyl alcohol.

Aspect 17. The urinary catheter of any one of aspects 15-16 wherein the plasticizing agent comprises water.

Aspect 18. The urinary catheter of any one of aspects 15-17 wherein the plasticizing agent comprises a non-solvent for polyvinyl alcohol.

Aspect 19. The urinary catheter of any one of aspects 15-18 wherein the plasticizing agent comprises propylene glycol.

Aspect 20. The urinary catheter of any one of aspects 15-16, wherein the plasticizing agent comprises of a mixture of a solvent and non-solvent for polyvinyl alcohol.

Aspect 21. The urinary catheter of aspect 20, wherein the ratio of the solvent to non-solvent is one of 100 vol % non-solvent and 0 vol % solvent: 90 vol % non-solvent and 10 vol % solvent; 80 vol % non-solvent and 20 vol % solvent; and 70 vol % non-solvent and 30 vol % solvent.

Aspect 22. The urinary catheter of any one of aspects 20-21 wherein the solvent comprises water.

Aspect 23. The urinary catheter of any one of aspects 20-22, wherein the non-solvent comprises propylene glycol.

Aspect 24. A urinary catheter, comprising: a catheter shaft having a first section comprised of polyvinyl alcohol and a first amount propylene glycol and a second section comprised of polyvinyl alcohol and a second amount of propylene glycol wherein the first section has a different stiffness from the second section.

Aspect 25. A method of making a catheter of varying stiffness comprising: immersing a first section of a catheter made from polyvinyl alcohol in a first plasticizing agent; and immersing a second section of the catheter made in a second plasticizing agent.

Aspect 26. The method of aspect 25 wherein the first and second plasticizing agents comprise mixtures of propylene glycol and water.

Aspect 27. The method of aspect 26 wherein the concentration of propylene glycol in the first plasticizing agent is different from that in the second plasticizing agent.

Aspect 28. The method of aspect 25 wherein the first plasticizing agent comprises propylene glycol, and the second plasticizing agent comprises a mixture of propylene glycol and water.

Aspect 29. The method of aspect 25 wherein the first and second plasticizing agents are the same and the first section of the catheter is immersed in the plasticizing agent for a first time period and the second section of the catheter is immersed in the plasticizing agent for a second time period which is different from the first time period.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A urinary catheter, comprising:
   a shaft consisting of polyvinyl alcohol and plasticizing agent, the shaft including a first section having a first stiffness and a second section having a second stiffness; wherein at least one of said sections is impregnated with the plasticizing agent, the plasticizing agent comprising propylene glycol.

2. The urinary catheter of claim 1, wherein the first section has greater stiffness than the second section.

3. The urinary catheter of claim 1, wherein the second section has a greater stiffness than the first section.

4. The urinary catheter of claim 1, wherein the first section is impregnated with the plasticizing agent.

5. The urinary catheter of claim 4, wherein the plasticizing agent lubricates the catheter.

6. The urinary catheter of claim 1, wherein the second section is impregnated with the plasticizing agent.

7. The urinary catheter of claim 1, wherein the plasticizing agent further comprises a solvent for polyvinyl alcohol.

8. The urinary catheter of claim 7, wherein the plasticizing agent comprises water.

9. The urinary catheter of claim 7, wherein the ratio of the solvent to propylene glycol is one of 100 vol % propylene glycol and 0 vol % solvent; 90 vol % propylene glycol and 10 vol % solvent; 80 vol % propylene glycol and 20 vol % solvent; and 70 vol % propylene glycol and 30 vol % solvent.

10. The urinary catheter of claim 9, wherein the solvent comprises water.

11. The urinary catheter of claim 1, wherein
   the first section of the shaft having an amount of the plasticizing agent impregnated therein; and
   the second section of the shaft having a second amount of the plasticizing agent impregnated therein, wherein the second amount of the plasticizing agent is different from the first amount.

12. The urinary catheter of claim 11, wherein the plasticizing agent further comprises a solvent for polyvinyl alcohol.

13. The urinary catheter of claim 12, wherein the plasticizing agent comprises water.

14. A method of making a catheter of varying stiffness comprising:
   immersing a first section of a catheter consisting of polyvinyl alcohol in a first plasticizing agent; and
   immersing a second section of the catheter consisting of polyvinyl alcohol in a second plasticizing agent;
   wherein at least one of the first and second plasticizing agent comprises propylene glycol.

* * * * *